United States Patent
Patel

(10) Patent No.: US 9,619,623 B2
(45) Date of Patent: Apr. 11, 2017

(54) MOBILE DEVICE CASING FOR HEALTH MONITORING

(71) Applicant: AZOI INC, Sunnyvale, CA (US)

(72) Inventor: Hamish Patel, Ahmedabad (IN)

( * ) Notice: Subject to any disclaimer, the term of this patent is extended or adjusted under 35 U.S.C. 154(b) by 165 days.

(21) Appl. No.: 14/640,940

(22) Filed: Mar. 6, 2015

(65) Prior Publication Data

US 2015/0254414 A1 Sep. 10, 2015

(30) Foreign Application Priority Data

Mar. 6, 2014 (IN) .......................... 762/MUM/2014

(51) Int. Cl.
*A61B 5/00* (2006.01)
*G06F 19/00* (2011.01)
*A61B 5/0404* (2006.01)
*A61B 5/01* (2006.01)
*A61B 5/1455* (2006.01)
*A61B 5/08* (2006.01)
*A61B 5/0456* (2006.01)

(52) U.S. Cl.
CPC ........ *G06F 19/3418* (2013.01); *A61B 5/0404* (2013.01); *A61B 5/6898* (2013.01); *G06F 19/3406* (2013.01); *A61B 5/01* (2013.01); *A61B 5/0456* (2013.01); *A61B 5/08* (2013.01); *A61B 5/1455* (2013.01); *A61B 5/14551* (2013.01); *A61B 5/7203* (2013.01); *A61B 5/7275* (2013.01); *A61B 2562/06* (2013.01)

(58) Field of Classification Search
CPC ..... A61B 2562/06; A61B 5/01; A61B 5/0404; A61B 5/0456; A61B 5/08; A61B 5/1455; A61B 5/14551; A61B 5/6898; A61B 5/7203; A61B 5/7275; G06F 19/3406; G06F 19/3418
See application file for complete search history.

(56) References Cited

U.S. PATENT DOCUMENTS

2011/0056491 A1\* 3/2011 Rumph ............. A61M 16/0051
128/203.14

\* cited by examiner

*Primary Examiner* — George Manuel
(74) *Attorney, Agent, or Firm* — The Law Office of Austin Bonderer, PC; Austin Bonderer

(57) ABSTRACT

A casing adapted to use with a mobile device for monitoring health condition of a user is provided. The casing includes (a) a memory unit, (b) a sensor unit at a surface of the casing, (c) a plurality of health parameter measuring sensors embedded within the sensor unit for measuring raw health parameters data of the user, (d) a processor which is activated from a sleep mode based on a user input including contacting at least one predetermined sensor surface on the casing for a predetermined period, and (e) a power unit for controllably supplying power to the sensors and the processor upon detecting the user input. The processor (i) initializes and configures the sensors, and (ii) receives the raw health parameters data from the sensors. The casing further includes a communication unit for communicating the raw health parameters data to a mobile device for processing.

13 Claims, 14 Drawing Sheets

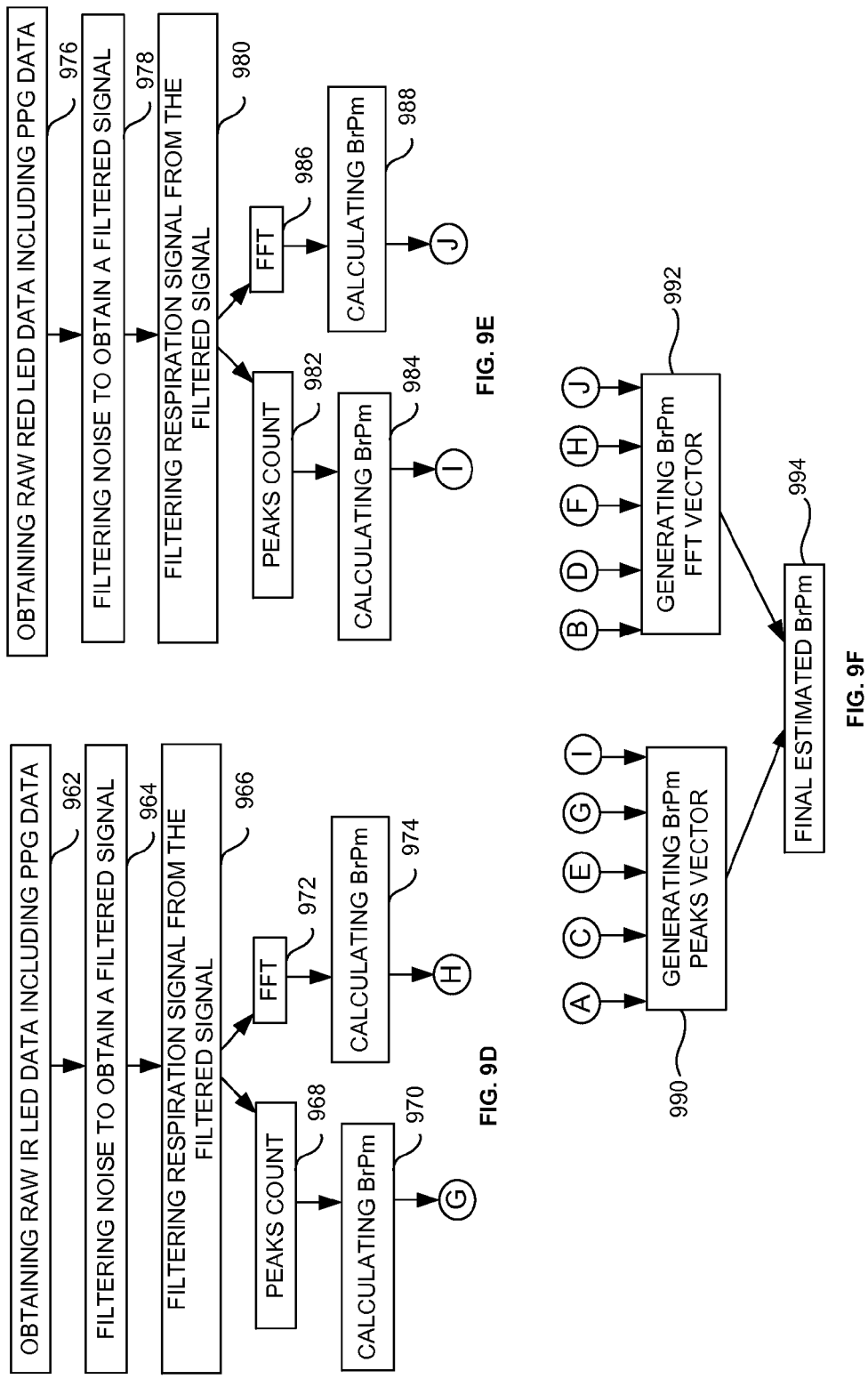

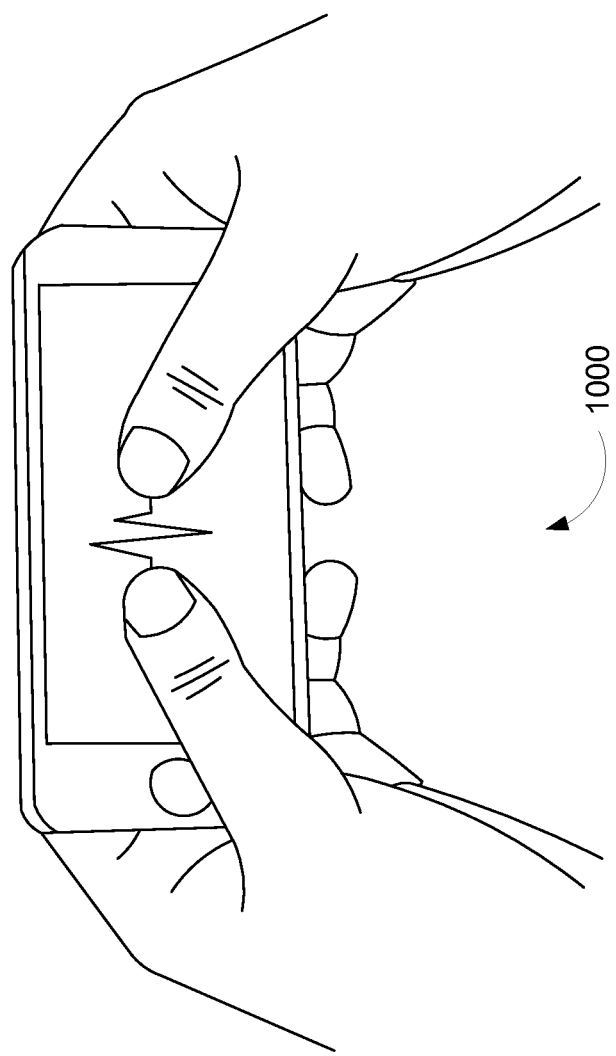

MOBILE DEVICE CASING FOR HEALTH MONITORING

CROSS-REFERENCE TO RELATED APPLICATIONS

This application claims priority to Indian patent application no. 762/MUM/2014 filed on Mar. 6, 2014, the complete disclosure of which, in its entirety, is herein incorporated by reference.

BACKGROUND

Technical Field

The embodiments herein generally relate to a health monitoring system, and more particularly to, a casing which is adapted to use with a mobile device for monitoring health condition of a user.

Description of the Related Art

Advancement in a medical science helps users to assess health conditions. The aim of a medical fraternity off late has also been to educate people on the value of getting the diseases diagnosed at preliminary stages by regular check-ups to ascertain their health conditions. Many health monitoring devices are made available to measure the health conditions. Few such devices include pedometer, pulse monitor, oxygen saturation and monitor that are available in a market through which a user monitors his/her health parameters. However, with the existing devices, a user can measure only one health parameter at a time using a device which is designed for measuring that particular health parameter. But having information on multiple health parameters provides a vital data on overall health condition of a user as well as functioning of individual parts of the user. Typically a user has to own multiple devices for measuring various health parameters of the user. For example, a pedometer for counting user motion and a pulse monitor for measuring pulse of the user. Hence, there is a need for monitoring multiple health parameters of a user at a time using a single device.

One approach to address the above problem is to combine all the devices functionality into a single device. However, such device requires more hardware components, spatial arrangement, and accordingly size of the device is also large. Hence, handling of the device is difficult for a user. Accordingly, there remains a need for a device that measures multiple health parameters of a user at a time and accommodates health parameters measuring unit within a limited space.

SUMMARY

In view of the foregoing, an embodiment herein provides a casing adapted to use with a mobile device for monitoring health condition of a user. The casing includes (a) a memory unit, (b) a sensor unit at a surface of the casing, (c) a plurality of health parameter measuring sensors embedded within the sensor unit for measuring raw health parameters data of the user, (d) a processor which is activated from a sleep mode based on a user input including contacting at least one predetermined sensor surface on the casing for a predetermined period, and (e) a power unit for controllably supplying power to the sensors and the processor upon detecting the user input. The processor (i) initializes and configures the sensors, and (ii) receives the raw health parameters data from the sensors. The casing further includes a communication unit for communicating the raw health parameters data to a mobile device for processing. The casing may further include a connector port for connecting at least one external sensor to communicate with the processor.

In another embodiment, a system for monitoring health condition of a user is provided. The system includes a casing and a mobile device. The casing includes (a) a memory unit, (b) a sensor unit at a surface of the casing, (c) a plurality of health parameter measuring sensors embedded within the sensor unit for measuring raw health parameters data of the user, (d) a processor which is activated from a sleep mode based on a user input including contacting at least one predetermined sensor surface on the casing for a predetermined period, and (e) a power unit for controllably supplying power to the sensors and the processor upon detecting the user input. The processor (i) initializes and configures the sensors, and (ii) receives the raw health parameters data from the sensors. The casing further includes a communication unit for communicating the raw health parameters data to the mobile device for processing. The health parameter measuring sensors include a temperature sensor, electrocardiogram (ECG) electrodes, and a blood oxygen level measuring sensor.

The mobile device adapted to use with the casing includes (i) a memory unit including a database and a set of modules, and (ii) a processor that executes the set of modules. The set of modules include a raw health parameters data receiving module and a raw data processing module including an ECG data processing module. The raw health parameters data receiving module receives the raw health parameters data from the communication unit. The ECG data processing module (a) filters baseline wandering from the raw health parameters data to obtain a filtered health parameter data, (b) detects a plurality of peaks that are within a predetermined peak range from the filtered health parameter data, (c) calculates an average interval of successive peaks of the plurality of peaks, and (d) calculates a heart rate of the user based on the average interval of the successive peaks.

The set of modules may further include an oxygen saturation computing module that (a) obtains photoplethysmogram (PPG) data including signals from an infrared light emitting diode and a red light emitting diode from the communication unit, (b) determines a peak buffer containing peaks of the PPG data, (c) calculates a peak to peak amplitude of values sampled by a photodiode, and (d) determines saturation of peripheral oxygen (SpO2) based on the peak to peak amplitude. The set of modules may further include a respiration data processing module that processes the PPG data or the ECG data and measures respiration characteristic of the user. The set of modules further include a temperature computing module that computes skin temperature of the user from the raw health parameters data including voltage values. The casing may further include a connector port for connecting at least one external sensor to communicate with the processor. The casing may be in a form of a wrist watch, a band, or a cover.

In yet another embodiment, a method for monitoring health condition of a user using a casing adapted to use with a mobile device is provided. The method includes (i) obtaining, by a processor of the casing, a user input including contacting at least one predetermined sensor surface on the casing for a predetermined period, (ii) activating the processor of the casing from a sleep mode based on the user input, (iii) initializing and configuring, by the processor, a plurality of health parameter measuring sensors which is embedded with the casing, (iv) measuring, by the plurality of health parameter measuring sensors, raw health parameters data of the user, (v) receiving, by the processor, the raw health parameters data from the plurality of health parameter measuring sensors, and (vi) communicating, by a communication unit, the raw health parameters data to the mobile device for processing.

At least one external sensor may be connected to the processor through a connector port. The method may further include (a) filtering, by a processor of the mobile device, baseline wandering from the raw health parameters data to obtain a filtered health parameter data, (b) detecting, by the processor of the mobile device, a plurality of peaks that are within a predetermined peak range from the filtered health parameter data, (c) calculating, by a processor of the mobile device, an average interval of successive peaks of the plurality of peaks, and (d) calculating, by a processor of the mobile device, a heart rate of the user based on the average interval of the successive peaks. The method may further include (a) obtaining photoplethysmogram (PPG) data from the communication unit, (b) determining a peak buffer containing peaks of the PPG data, (c) calculating a peak to peak amplitude of values sampled by a photodiode, and (d) determining saturation of peripheral oxygen (SpO2) based on the peak to peak amplitude. The PPG data or the ECG data may be processed and thereby respiration characteristic of the user may be measured. Skin temperature of the user may be computed from the raw health parameters data including voltage values.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 9D is a flow diagram illustrates methods for computing a seventh BrPm and a eighth BrPm of the user from raw infrared light emitting diode (IR LED) data obtained from an IR LED of the casing using the respiration data processing module of FIG. 4 according to an embodiment herein;

FIG. 9E is a flow diagram illustrates methods for computing a ninth BrPm and a tenth BrPm of the user from raw red light emitting diode (RED LED) data obtained from a RED LED of the casing using the respiration data processing module of FIG. 4 according to an embodiment herein;

FIG. 9F is a flow diagram illustrating a method for computing a final BrPm of the user using the respiration data processing module of FIG. 4 according to an embodiment herein;

FIG. 10 is an exemplary view illustrating a user interface view of the mobile device displaying health condition of the user in analytics chart according to an embodiment herein;

DETAILED DESCRIPTION OF PREFERRED EMBODIMENTS

Figure 1:
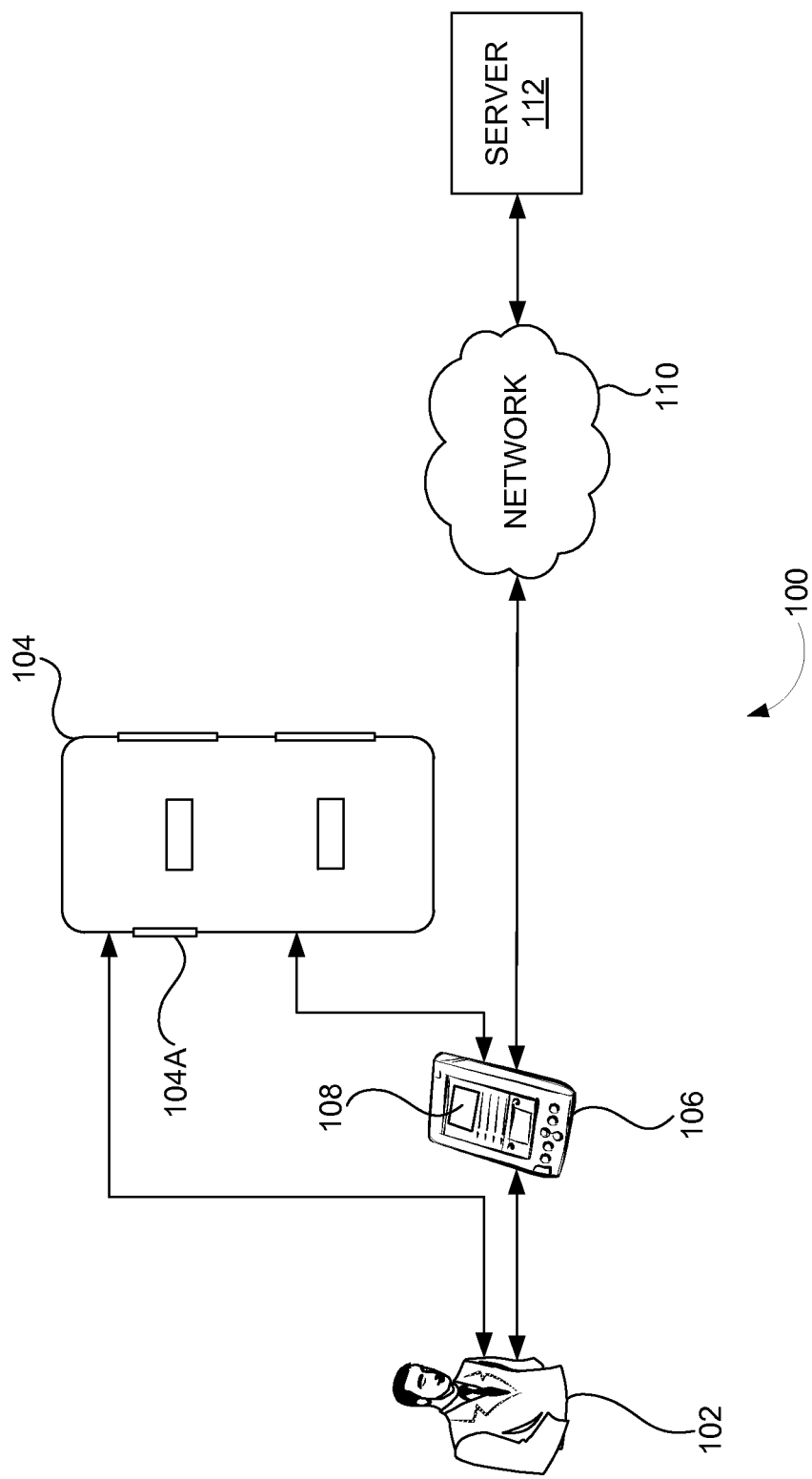
FIG. 1 is a system view illustrates a user interacting with a casing which is adapted to use with a mobile device for monitoring health condition of the user according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a device that measures multiple health parameters of a user at a time and accommodates health parameters measuring unit within a limited space. The embodiments herein achieve this by providing a casing that is adapted to use with a mobile device for monitoring health condition of a user. The casing includes a main module with one or more sensors to record one or more statistics associated with health condition of a user. Referring now to the drawings, and more particularly to FIGS. 1 through 13, where similar reference characters denote corresponding features consistently throughout the figures, there are shown preferred embodiments.

FIG. 1 is a system view illustrates a user 102 interacting with a casing 104 which is adapted to use with a mobile device 106 for monitoring health condition of the user 102 according to an embodiment herein. The system view further includes a health monitoring application 108, a network 110, and a server 112. The casing 104 is configured to enclose the mobile device 106. The casing 104 includes multiple sensors for measuring various health related parameters of the user 102. The casing 104 is of any physical form including a cover for the mobile device 106. The casing 104 includes a universal connector 104A. The universal connector 104A enables one or more external sensors (e.g., a spirometry or a glucose sensor) to communicate with a microcontroller of the casing 104 over certain protocol (e.g., $I^2C$). In one embodiment, one or more external sensors connected to the casing 104 through the universal connector 104A monitors health condition of the user 102 and communicate to the server 112 for analysis.

The casing 104 further includes a sensor unit in which the multiple sensors (e.g., pulse oxygen/blood pressure sensor, a temperature sensor, and an ECG electrode) are embedded. Surface of the casing 104 includes one or more predetermined sensor surfaces. When the user 102 contacts a predetermined sensor surface from the one or more predetermined sensor surfaces of the casing 104 for a predetermined period, a sensor associated with the predetermined sensor surface is activated for measuring health parameter of the user 102. In one embodiment, all the sensors in the sensor unit are activated by contacting a predetermined surface of the casing 104 for a predetermined period. The sensors embedded within the sensor unit measures raw health parameters data of the user 102 which requires processing. For example, one or more raw health parameters data captured by the sensors include (i) a pulse rate, (ii) a heart variability rate, (iii) a blood pressure range, (iv) temperature range, (v) oxygen saturation, and/or (vi) a ECG are monitored. The casing 104 communicates the raw health parameters data to the mobile device 106 for processing. In one embodiment, the casing 104 communicates the raw health parameters to the mobile device 106 through Bluetooth.

In one embodiment, the mobile device 106 is a smart phone, a laptop, a tablet PC, a smart device, and/or an ultra-book, etc. The mobile device 106 includes the health monitoring application 108 which receives raw health parameters data from the casing 104, and perform analysis to obtain health condition of the user 102. In one embodiment, health condition of the user 102 is displayed as a health analytics chart. In one embodiment, analysis of the raw health parameters data is performed at a processor of the casing 104 to obtain health condition of the user 102.

In one embodiment, information associated with health condition of the user 102 is captured at regular intervals (e.g., on daily basis or twice a day). The mobile device 106 is synchronized with the server 112 through the network 110. In one embodiment, the network 110 may be an internet, or a broadcast network, or a wireless network (e.g., an infrared, a general packet radio service (GPRS), a Bluetooth™, Wi-Fi, and/or 3G). The vital signs that are captured at the moment in conjunction with past data collected may be helpful to show person's present health status, in an example embodiment. The server 112 stores history associated with a health condition of the user 102. Similarly, the server 112 receives health condition of a plurality of users from their corresponding devices, and stores in a database. The consolidated data of vital signs of different users may be helpful to find common patterns of different types of diseases and illness. In one embodiment, the server 112 runs an analytic algorithm to predict illness and notify users about important information to his/her mobile phone or on a web interface.

Figure 2:
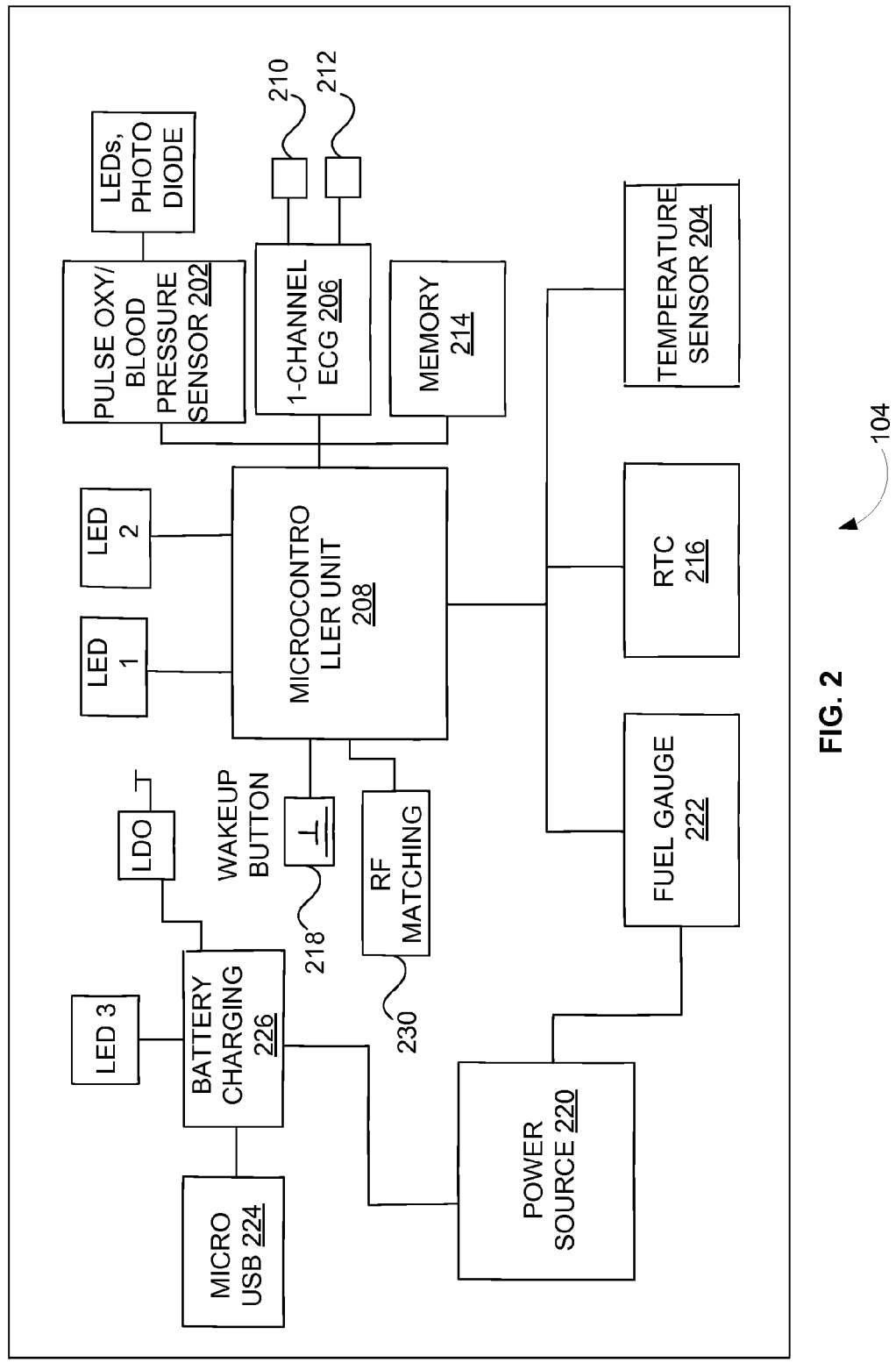
FIG. 2 illustrates an exploded view of the casing of FIG. 1 according to an embodiment herein.

FIG. 2 illustrates an exploded view of the casing 104 of FIG. 1 according to an embodiment herein. The casing 104 includes a sensor unit (shown in the FIG. 3) which includes various sensors. The sensor unit is placed at any surface of the casing 104. Examples of such sensor include a pulse oxygen or blood pressure sensor 202, a temperature sensor 204, an ECG electrode 206, and a microcontroller unit 208. In one embodiment, the casing 104 includes one or more sensors which are embedded inside a main module which can be placed or removed from a cavity portion. In one embodiment, the pulse oxygen/blood pressure sensor 202 is made of LEDs and one or more photo diodes that measures health condition of a patient (e.g., a pulse rate, an oxygen saturation level, and/or a blood pressure range). The temperature sensor 204 obtains signals related to body temperature of the user 102. In one embodiment, the casing 104 includes the temperature sensor 204 is a contactless infrared (IR) sensor which obtains temperature signals without need for the user 102 to contact a sensor surface on the casing 104.

The ECG electrode 206 includes one or more electrode cardiogram sensors. In one embodiment, the casing 104 includes a first electrode 210 and a second electrode 212 at a surface of the casing 104. When the user 102, places his/her finger on the first electrode 210 and the second electrode 212, the ECG electrode 206 obtains signal related to cardio functionality of the user 102. Other examples of sensors embedded within the sensor unit include a heart rate measuring sensor, a stress computing sensor, a urine analysis sensor, etc. The signals including raw health parameters data from sensors of the casing 104, and associated statistics are stored in a database (a memory 214). In one embodiment, the memory 214 stores health related information of the user 102. Signals including raw health parameters data are time-stamped by the real-time-clock (RTC) unit 216.

The microcontroller unit 208 is a chipset (e.g., a microcontroller or a processor such as a processing unit) which has complete controls of commands for operating sensors, receiving signals including raw health parameters data from the sensors, and communicating the signals to the mobile device 106 for processing. By default, the microcontroller is in a sleep mode for saving power. When the user 102 contacts one or more predetermined sensor surface of the casing 104 for a predetermined period, a wakeup button 218 is activated, and in turn activates the microcontroller unit 208 from the sleep mode. The microcontroller unit 208 initializes, configures, and activates sensors of the casing 104, and receives raw health parameters data from the sensors of the casing 104. The microcontroller unit 208 communicates a required action to be taken by the user 102 to the mobile device 106 based on signals obtained from sensors of the casing 104. In one embodiment, the microcontroller unit 208 communicates the raw health parameters data to the mobile device 106 in real-time, near-real-time, or at every predetermined time interval.

The casing 104 further includes a power source 220. The power source may be a rechargeable battery to provide power to components for performing various functions. The power source may be any other source, but not limited to, such as a solar cell, in one example embodiment. The power source 220 is capable of controllably providing power to sensors and the microcontroller unit 208 upon detecting a user input including contacting one or more predetermined sensor surface of the casing 104 for a predetermined period. In one embodiment, the power source 220 supplies less power to the microcontroller unit 208 when it is in a sleep mode, and supplies more power to the microcontroller unit 208 when it is activated. The fuel gauge 222 indicates remaining available power at the power source 220. The casing 104 further includes a USB port 224 for connecting external devices (e.g., a battery charger 226), and a communication unit 228 (not shown in the FIG. 2). The communication unit 228 communicates raw health parameters data obtained from one or more sensors of the casing 104 to the mobile device 106 for processing. The casing 104 further includes a radio frequency matched 230 for matching RF signals.

Figure 3:
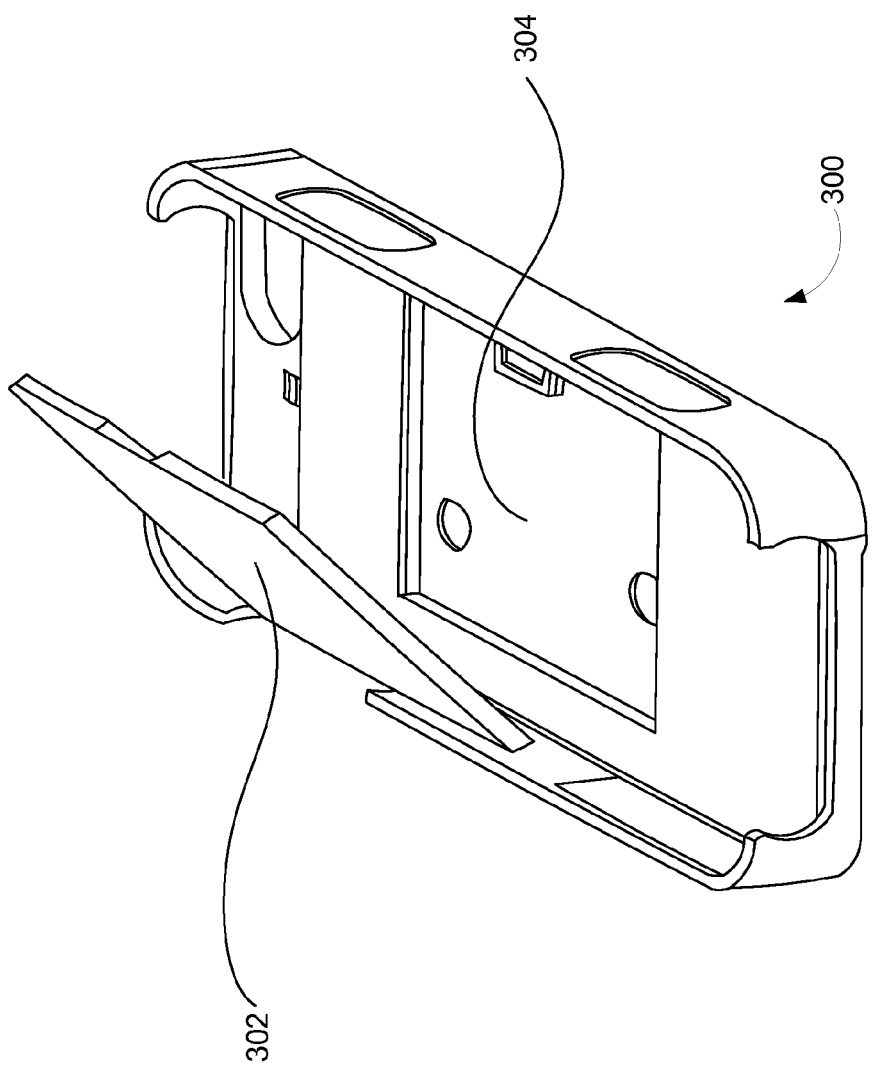
FIG. 3 illustrates an exemplary view of a health monitoring system including the casing of FIG. 1 which is adapted to use with a mobile device according to an embodiment herein.

FIG. 3 illustrates an exemplary view 300 of a health monitoring system including the casing 104 of FIG. 1 which is adapted to use with a mobile device (e.g., a smartphone) according to an embodiment herein. One or more sensors are embedded within a sensor unit 302 which can be placed or removed from a cavity portion 304. The casing 104 is adapted to use with any mobile device irrespective of size of the mobile device 106.

Figure 4:
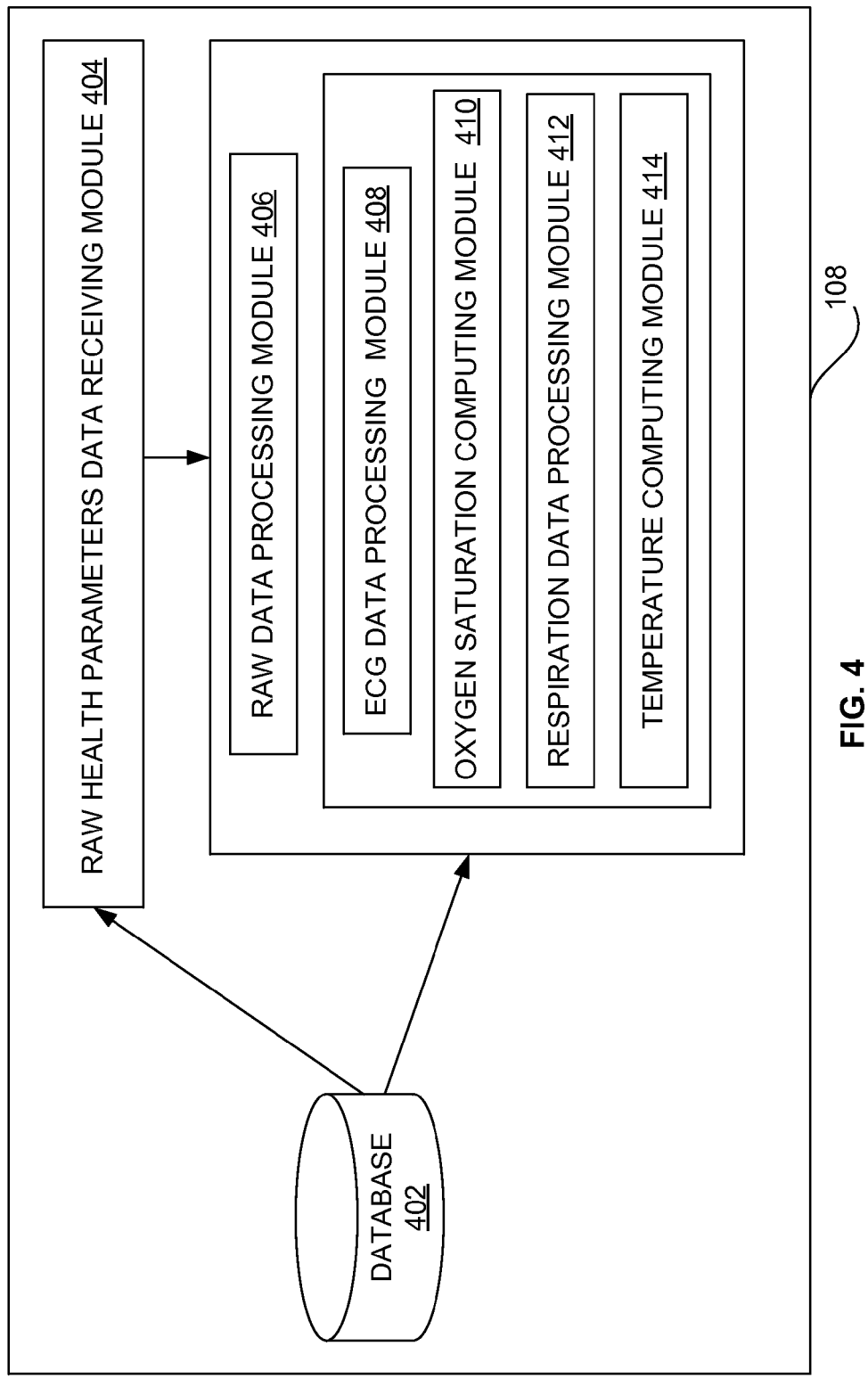
FIG. 4 is an exploded view of a health monitoring application of the mobile device of FIG. 1 according to an embodiment herein.

FIG. 4 is an exploded view of the health monitoring application 108 of the mobile device 106 of FIG. 1 according to an embodiment herein. The health monitoring application 108 includes a database 402, a raw health parameters data receiving module 404, and a raw data processing module 406. The raw health parameters data receiving module 404 receives raw health parameters data that are measured by sensors of the casing 104 from the communication unit 228. The raw data processing module 406 obtains raw health parameters data from the raw health parameters data receiving module 404, and processes the data to obtain health condition of the user 102. The raw data processing module 406 includes one or more sub-modules for processing the raw health parameters data. In one embodiment, the sub-modules are customized according to context of the user. In another embodiment, the sub-modules are in-built. Based on a type of data that are obtained by the raw health parameters data receiving module 404, the one or more sub-modules process the data for obtaining health condition of the user 102. The sub-modules include, but not limited to, an ECG data processing module 408, an oxygen saturation computing module 410, a respiration data processing module 412, and/or a temperature computing module 414. The raw data processing module 406 includes at least one sub-module for processing any health related data of the user 102. Other examples of sub-modules include a stress data processing module, a pulse oximetry data processing module, a urine analysis data processing module, etc.

Figure 5:
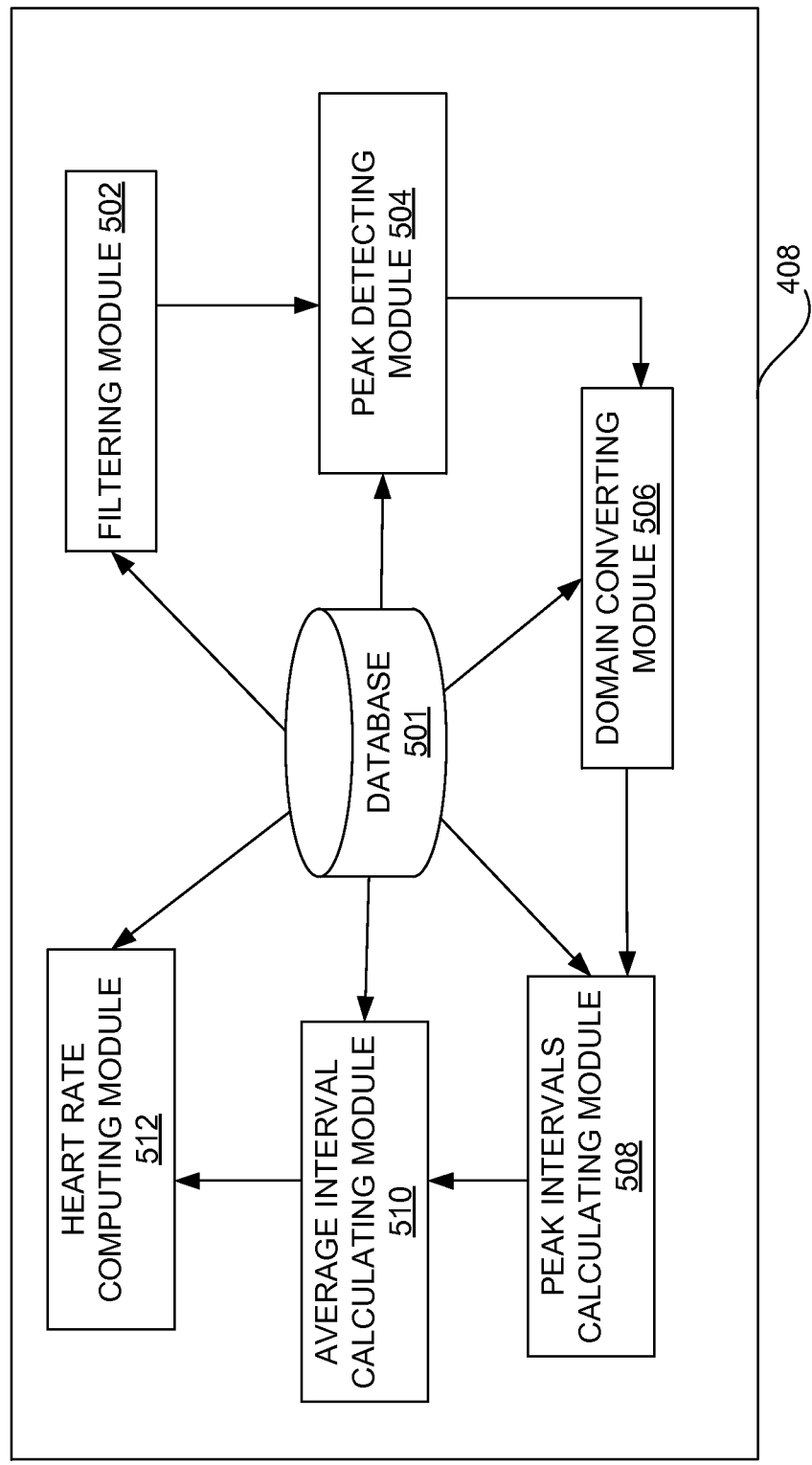
FIG. 5 is an exploded view of a ECG data processing module of a raw data processing module of FIG. 4 according to an embodiment herein.

FIG. 5 is an exploded view of the ECG data processing module 408 of the raw data processing module 406 of FIG. 4 according to an embodiment herein. The ECG data processing module 408 includes a database 501, a filtering module 502, a peak detecting module 504, a domain converting module 506, a peak intervals calculating module 508, an average interval calculating module 510, and a heart rate computing module 512.

Figure 6:
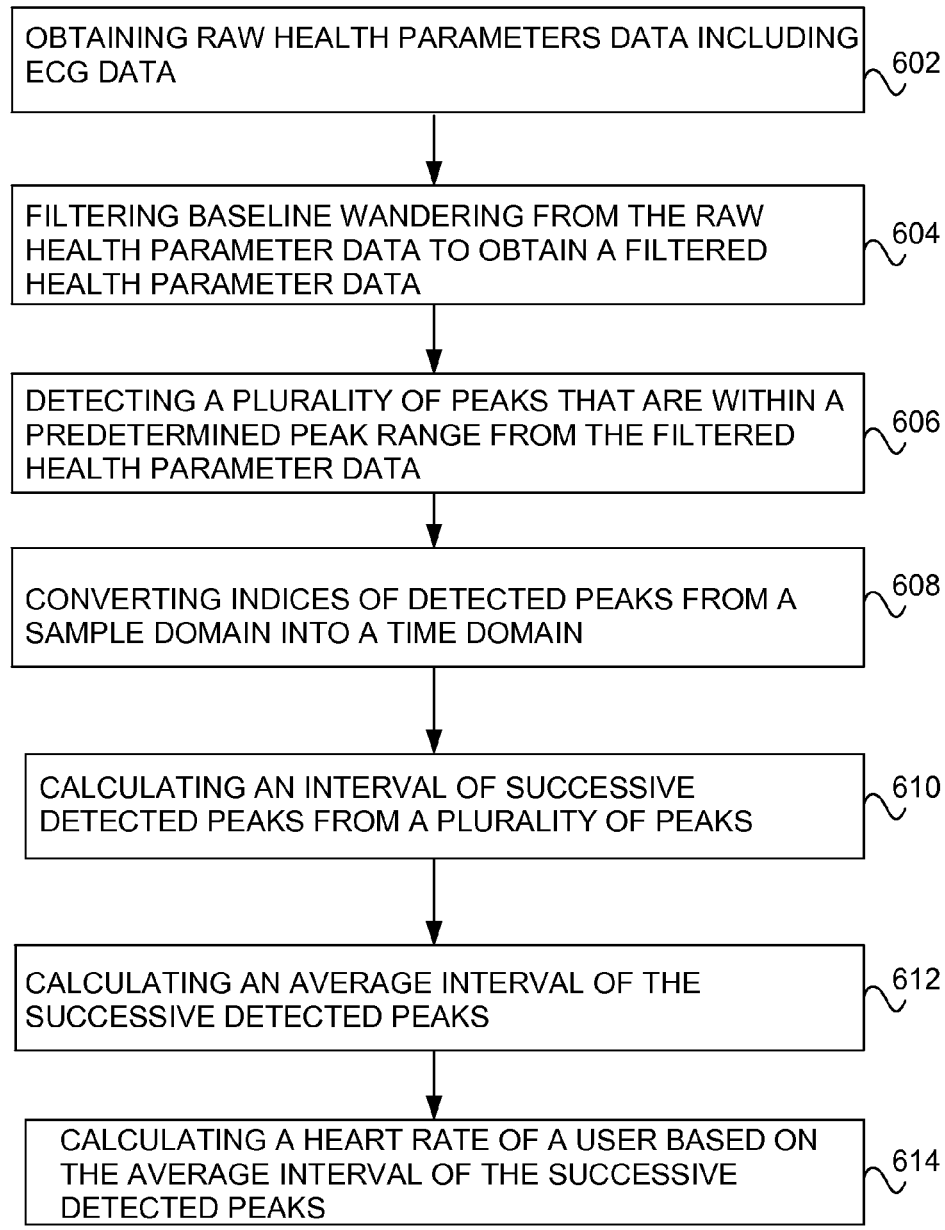
FIG. 6 is a flow diagram illustrating a method for measuring heart functionality of the user from raw health parameters data received by the mobile device from the casing using the ECG data processing module of FIG. 4 according to an embodiment herein.

FIG. 6 is a flow diagram illustrating a method for measuring heart functionality of the user 102 from raw health parameters data received by the mobile device 106 from the casing 104 using the ECG data processing module 408 of FIG. 4 according to an embodiment herein. In step 602, the ECG data processing module 408 obtains raw health parameters data including ECG data from the raw health parameters data receiving module 404. In step 604, the filtering module 502 filters baseline wandering from the raw health parameters data to obtain a filtered health parameter data. In step 606, the peak detecting module 504 detects a plurality of peaks that are within a predetermined peak range from the filtered health parameter data. For example, when the predetermined peak range is 30 to 200 beats per minute, the peak detecting module 504 detects peaks that are only within 30 to 200 beats per minute. In step 608, the domain converting module 506 converts indices of detected peaks from a sample domain into a time domain. In step 610, the peak intervals calculating module 508 calculates an interval of successive detected peaks from a plurality of peaks. In step 612, the average interval calculating module 510 calculates an average interval of the successive detected peaks. In step 614, the heart rate computing module 512 calculates a heart rate of the user 102 based on the average interval of the successive detected peaks in accordance with an equation Heart rate=60/Average interval, in one example embodiment.

Figure 7:
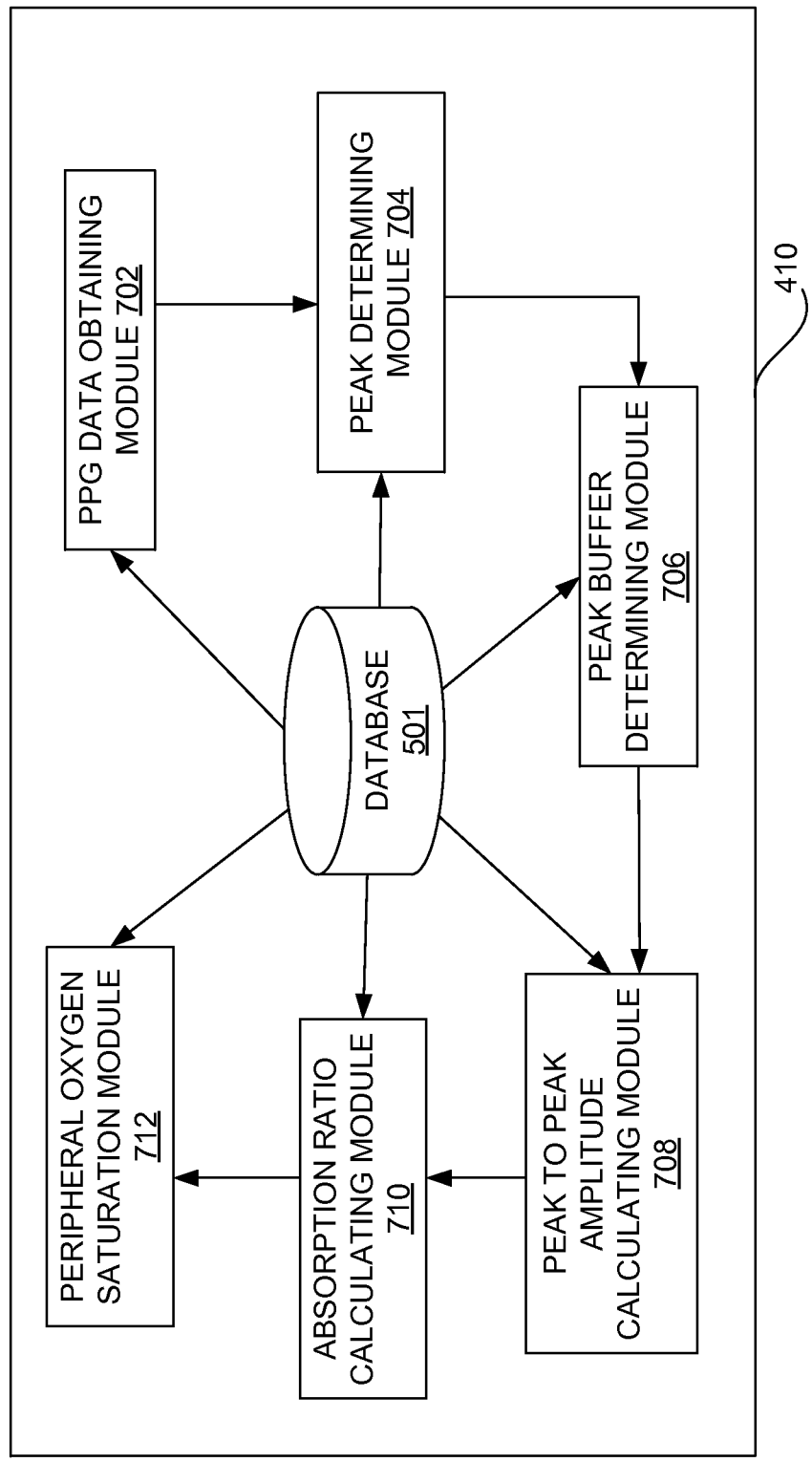
FIG. 7 is an exploded view of an oxygen saturation computing module of a raw data processing module of FIG. 4 according to an embodiment herein.

FIG. 7 is an exploded view of the oxygen saturation computing module 410 of the raw data processing module 406 of FIG. 4 according to an embodiment herein. The oxygen saturation computing module 410 includes a photoplethysmogram (PPG) data obtaining module 702, a peak determining module 704, a peak buffer determining module 706, a peak to peak amplitude calculating module 708, an absorption ratio calculating module 710, and a peripheral oxygen saturation module 712.

Figure 8:
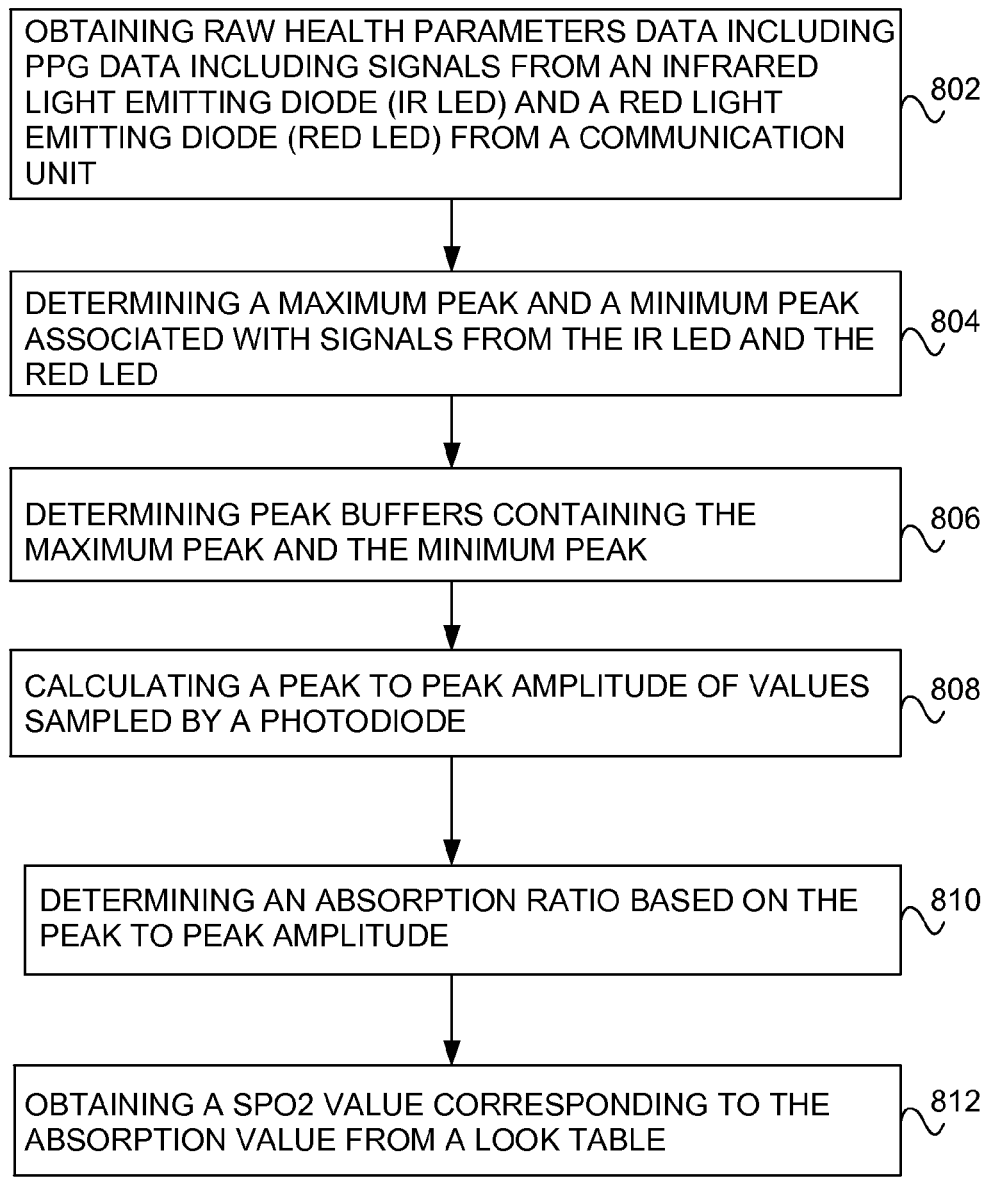
FIG. 8 is a flow diagram illustrating a method for measuring saturation of peripheral oxygen (SpO2) from raw health parameters data received by the mobile device from the casing using the oxygen saturation computing module of FIG. 4 according to an embodiment herein.

FIG. 8 is a flow diagram illustrating a method for measuring saturation of peripheral oxygen (SpO2) from raw health parameters data received by the mobile device 106 from the casing 104 using the oxygen saturation computing module 410 of FIG. 4 according to an embodiment herein. In step 802, the photoplethysmogram (PPG) data obtaining module 702 obtains raw health parameters data including PPG data including signals from an infrared light emitting diode and a red light emitting diode from the communication unit 228. In step 804, the peak determining module 704 determines a maximum peak and a minimum peak associated with signals from the IR LED and the RED LED. The peak determining module 704 determines the maximum peak by determining a peak which has value remains high till absorption reaches a predetermined threshold value. Similarly, the peak determining module 704 determines the minimum peak by determining a peak which has value remains low till absorption reaches a predetermined threshold value. In step 806, the peak buffer determining module 706 determines peak buffers containing the maximum peak and the minimum peak. In step 808, the peak to peak amplitude calculating module 708 calculates peak to peak amplitude of values sampled by a photodiode. In step 810, the absorption ratio calculating module 710 determines an absorption ratio based on the peak to peak amplitude in accordance with an equation (RedAC/RedDC)/(IrAC/IrDC). In step 812, the peripheral oxygen saturation module 712 obtains a SpO2 value corresponding to the absorption value from a look table. In one embodiment, oxygen saturation is defined as measurement of amount of oxygen dissolved in blood, based on a detection of hemoglobin and deoxyhemoglobin. Two different light wavelengths (e.g., IR LED and RED LED) are used to measure actual difference in absorption spectra of oxyhemoglobin (HbO2) and hemoglobin (Hb). The bloodstream is affected by a concentration of HbO2 and Hb, and their absorption coefficients are measured using two wavelengths 660 nm (red light spectra) and 940 nm (infrared light spectra). Deoxygenated and oxygenated hemoglobin absorb different wavelengths. Deoxygenated hemoglobin (Hb) has a higher absorption at 660 nm and oxygenated hemoglobin (HbO2) has a higher absorption at 940 nm. The respiration data processing module 412 computes a respiration rate of the user 102 based on raw health parameters data including the ECG and the PCG data as described in the FIG. 9.

With reference to FIGS. 9A through 9E, FIG. 9A is a flow diagram illustrates methods for computing a first BrPm and a second BrPm of the user 102 from R amplitude peaks of ECG data using the respiration data processing module 412 of FIG. 4 according to an embodiment herein. In step 902, raw health parameters data including ECG data is obtained by the mobile device 106 from the casing 104. In step 904, a baseline wandering is removed from the ECG data to obtain a filtered ECG data. In step 906, R peak indices are obtained from the filtered ECG data. In step 908, R amplitude peaks are derived from the R peak indices. In step 910, the R amplitude peaks are verified. In step 912, a cubic spline is interpolated for the R amplitude peaks. In step 914, peak counts are obtained from the R amplitude peaks. In step 916, a first BrPm is calculated. In step 918, fast Fourier transform is performed on the R amplitude peaks. In step 920, a second BrPm is calculated.

Figures 9A, 9B, 9C:
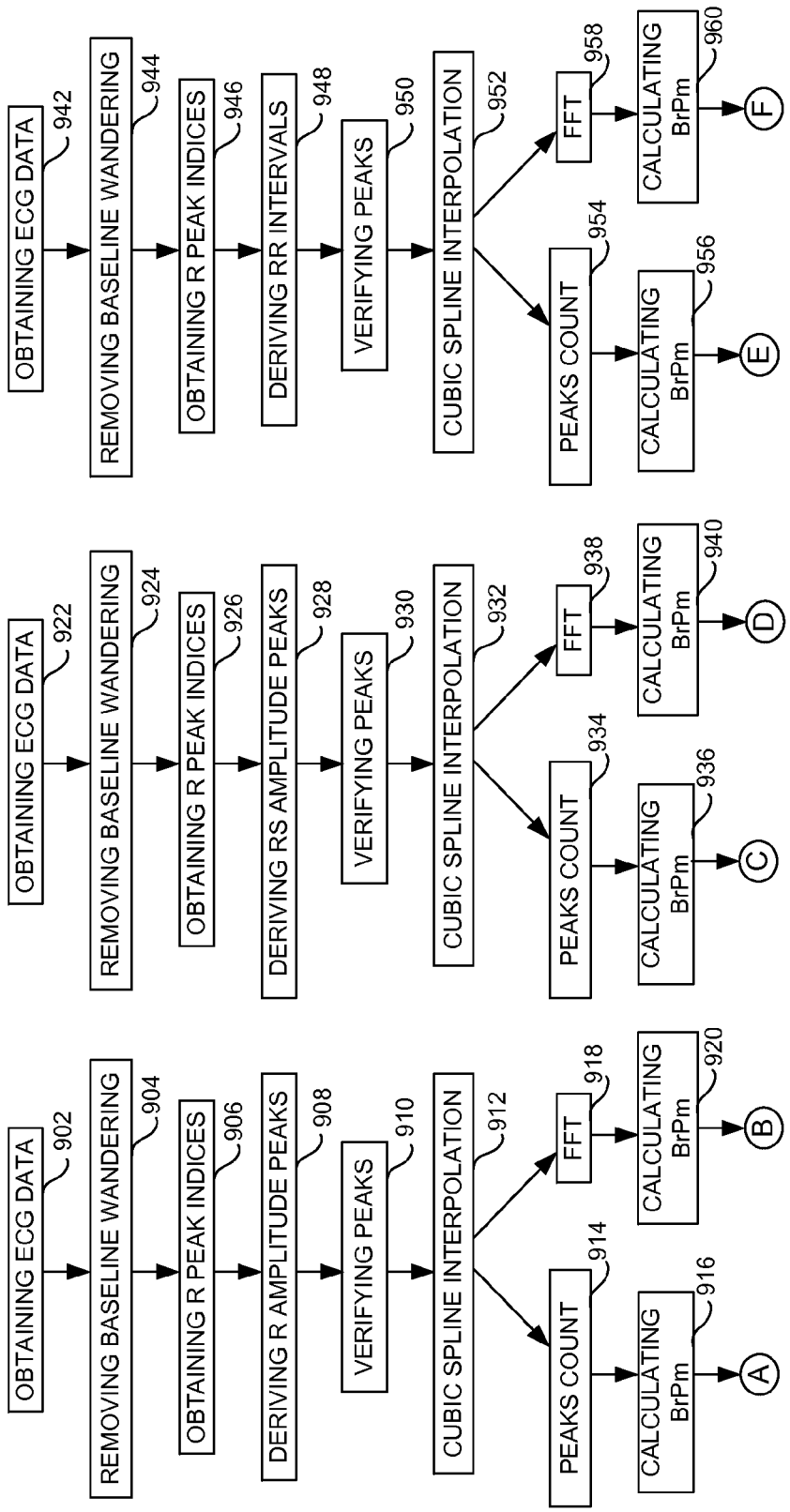
FIG. 9A is a flow diagram illustrates methods for computing a first BrPm and a second BrPm of the user from R amplitude peaks of ECG data using the respiration data processing module of FIG. 4 according to an embodiment herein.
FIG. 9B is a flow diagram illustrates methods for computing a third BrPm and a fourth BrPm of the user from RS amplitude peaks of ECG data using the respiration data processing module of FIG. 4 according to an embodiment herein.
FIG. 9C is a flow diagram illustrates methods for computing a fifth BrPm and a sixth BrPm of the user from RR intervals of ECG data using the respiration data processing module of FIG. 4 according to an embodiment herein.

FIG. 9B is a flow diagram illustrates methods for computing a third BrPm and a fourth BrPm of the user 102 from RS amplitude peaks of ECG data using the respiration data processing module 412 of FIG. 4 according to an embodiment herein. In step 922, raw health parameters data including ECG data is obtained by the mobile device 106 from the casing 104. In step 924, a baseline wandering is removed from the ECG data to obtain a filtered ECG data. In step 926, R peak indices are obtained from the filtered ECG data. In step 928, RS amplitude peaks are derived from the R peak indices. In step 930, the RS amplitude peaks are verified. In step 932, a cubic spline is interpolated for the RS amplitude peaks. In step 934, peak counts are obtained from the RS amplitude peaks. In step 936, a third BrPm is calculated. In step 938, fast Fourier transform is performed on the RS amplitude peaks. In step 940, a fourth BrPm is calculated.

Similarly, FIG. 9C is a flow diagram illustrates methods for computing a fifth BrPm and a sixth BrPm of the user 102 from RR intervals of ECG data using the respiration data processing module 412 of FIG. 4 according to an embodiment herein. In step 942, raw health parameters data including ECG data is obtained by the mobile device 106 from the casing 104. In step 944, a baseline wandering is removed from the ECG data to obtain a filtered ECG data. In step 946, R peak indices are obtained from the filtered ECG data. In step 948, RR intervals are derived from the R peak indices. In step 950, the RR intervals are verified. In step 952, a cubic spline is interpolated for the RR intervals. In step 954, peak counts are obtained from the RR intervals. In step 956, a fifth BrPm is calculated. In step 958, fast Fourier transform is performed on the RR intervals. In step 960, a sixth BrPm is calculated.

FIG. 9D is a flow diagram illustrates methods for computing a seventh BrPm and a eighth BrPm of the user 102 from raw infrared light emitting diode (IR LED) data obtained from an IR LED of the casing 104 using the respiration data processing module 412 of FIG. 4 according to an embodiment herein. In step 962, raw IR LED data including PPG data is obtained from an IR LED of the casing 104. In step 964, noise in the raw IR LED data is removed to obtain a filtered IR LED data. In step 966, respiration signal is filtered from the filtered IR LED data to obtain a filtered respiration signal. In step 968, peak counts are obtained from the filtered respiration signal. In step 970, a seventh BrPm is calculated. In step 972, fast Fourier transform is performed on the filtered respiration signal. In step 974, an eight BrPm is calculated.

FIG. 9E is a flow diagram illustrates methods for computing a ninth BrPm and a tenth BrPm of the user 102 from raw red light emitting diode (RED LED) data obtained from a RED LED of the casing 104 using the respiration data processing module 412 of FIG. 4 according to an embodiment herein. In step 976, raw RED LED data including PPG data is obtained from a RED LED of the casing 104. In step 978, noise in the raw RED LED data is removed to obtain a filtered RED LED data. In step 980, respiration signal is filtered from the filtered RED LED data to obtain a filtered respiration signal. In step 982, peak counts are obtained from the filtered respiration signal. In step 984, a ninth BrPm is calculated. In step 986, fast Fourier transform is performed on the filtered respiration signal. In step 988, a tenth BrPm is calculated.

FIG. 9F is a flow diagram illustrating a method for computing a final BrPm of the user 102 using the respiration data processing module 412 of FIG. 4 according to an embodiment herein. In step 990, a vector of BrPm peaks is generated based on BrPm values (i.e., a first BrPm, a third BrPm, a fifth BrPm, a seventh BrPm, and a ninth BrPm) derived from peak counts. In step 992, a vector of BrPm FFT is generated based on BrPm values (i.e., a second BrPm, a fourth BrPm, a sixth BrPm, a eight BrPm, and a tenth BrPm) derived from FFT. In step 994, an optimization algorithm receives the vector of BrPm peaks and the vector of BrPm FFT, and computes a final BrPm based on a trained weightage cumulative output corresponding to the vectors.

The temperature computing module 414 receives raw health parameters data from a temperature sensor of the casing 104. In one embodiment, the temperature sensor is a negative temperature coefficient (NTC) based temperature sensor which is connected to a ADC of the microcontroller unit 208. The raw data of temperature is voltage value. In one embodiment, the temperature computing module 414 computes resistance from the voltage value and mapped to a particular temperature using a look up table given by the NTC manufacturer for computing body temperature of the user 102.

FIG. 10 is an exemplary view 1000 illustrating a user interface view of the mobile device 106 displaying health condition of the user 102 in analytics chart according to an embodiment herein. The user 102 places his/her hands on a predetermined surface of the casing 104 to monitor his/her health condition. The health monitoring application 108 of the mobile device 106 further includes an analytics chart generation module (not shown in the FIG. 4) which generates a chart which depicts health condition of the user 102 based on analysis performed by the raw data processing module 406. In one embodiment, a plurality of charts each related to a health parameter (e.g., temperature, pulse oximetry, blood pressure, etc) are all displayed in a single user interface for the user 102 to conveniently to track his/her health condition.

Figure 11:
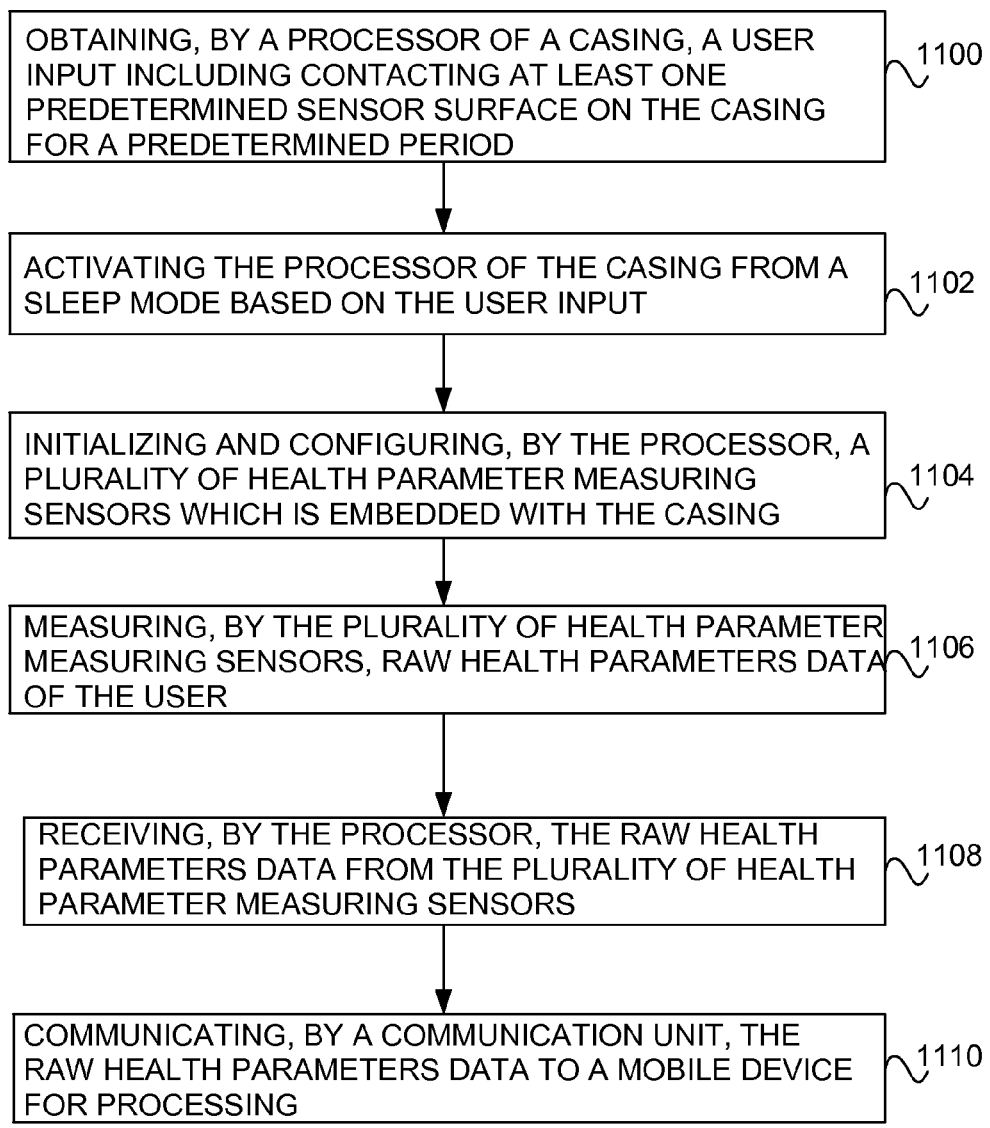
FIG. 11 is a flow diagram illustrating a method for monitoring health condition of the user using the casing adapted to use with the mobile device of FIG. 1 according to an embodiment herein.

FIG. 11 is a flow diagram illustrating a method for monitoring health condition of the user 102 using the casing 104 adapted to use with the mobile device 106 of FIG. 1 according to an embodiment herein. In step 1100, a user input including contacting at least one predetermined sensor surface on the casing 104 for a predetermined period is obtained by a processor (i.e., the microcontroller unit 208) of the casing 104. In step 1102, the processor of the casing 104 is activated from a sleep mode based on the user input. In step 1104, a plurality of health parameters measuring sensors which is embedded within the casing 104 is initialized and configured by the processor. In step 1106, raw health parameters data of the user 102 is measured by the plurality of health parameters measuring sensors. In step 1108, the raw health parameters data is received by the processor from the plurality of health parameters measuring sensors. In step 1110, the raw health parameters data is communicated to the mobile device 106 by the communication unit 228 for processing.

Figure 12:
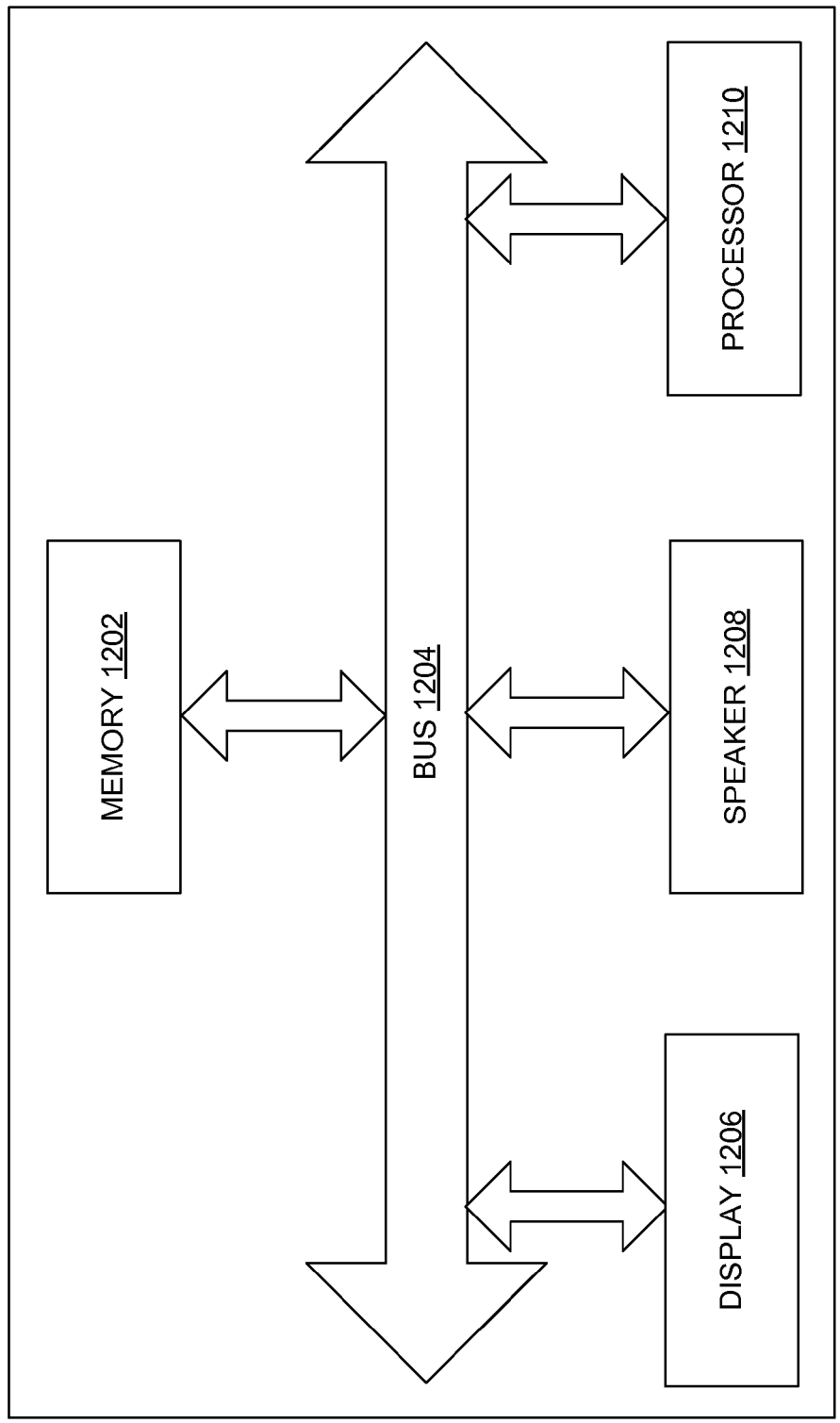
FIG. 12 illustrates a block diagram of the mobile device of FIG. 1 according to an embodiment herein.

FIG. 12 illustrates a block diagram of the mobile device 106 of FIG. 1 according to an embodiment herein. The mobile device 106 includes a memory 1202 having a set of instructions, a bus 1204, a display 1206, a speaker 1208, a processor 1210 capable of processing a set of instructions to perform any one or more of the methodologies herein, a microphone 1212, according to an embodiment herein. The processor may also enable digital content to be consumed in the form of video for output or audio for output via speaker and/or earphones 1208. The processor 1210 may also carry out the methods described herein and in accordance with the embodiments herein. The microphone 1212 is configured to process one or more inputs such as audio, voice, etc. and transmits to the microcontroller unit 208.

Digital content may also be stored in the memory 1202 for future processing or consumption. The memory 1202 may also store program specific information and/or service information (PSI/SI), including information about digital content (e.g., the detected information bits) available in the future or stored from the past. When digital content is selected, the processor 1210 may pass information. The content and PSI/SI may be passed among functions within the casing 104 using the bus 1204.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor. The embodiments herein can take the form of an entirely hardware embodiment, an entirely software embodiment or an embodiment including both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 13:
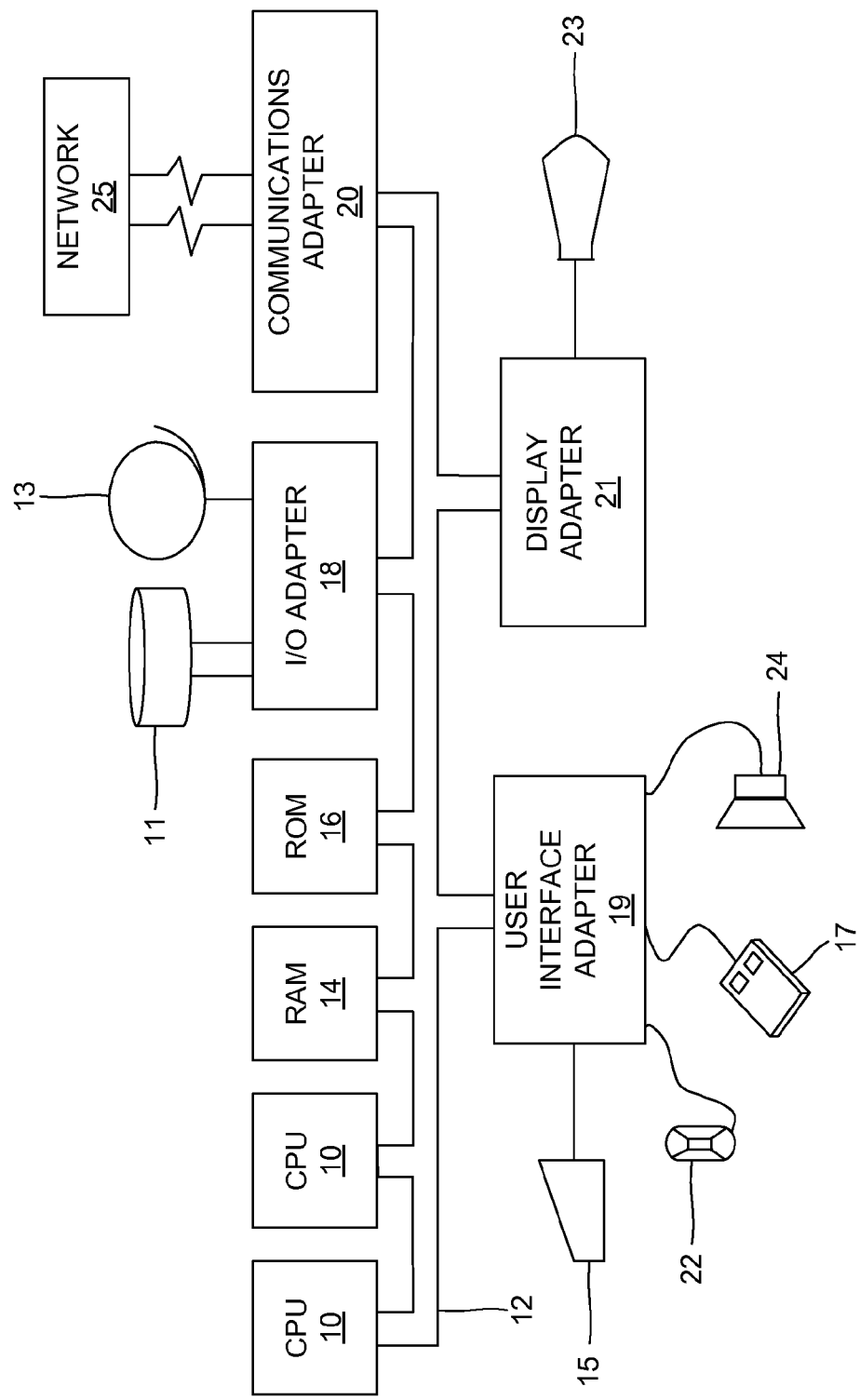
FIG. 13 depicting a representative hardware environment for practicing the embodiments herein.

A representative hardware environment for practicing the embodiments herein is depicted in FIG. 13. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The casing 104 enables monitoring one or more health related parameters including statistics data such as heart rate, body temperature, blood pressure, etc. using the one or more sensors. The casing 104 eliminates need of having different health monitoring systems to be carried with the user 102 for monitoring his/her health conditions. The health monitoring system allows a user to easily migrate to upgrade for any portable device without purchasing entire new phone cover (not necessary to buy entire new device).

The universal connector which enables external sensors to communicate with the microcontroller to monitor and communicate health conditions of a user over a communication protocol. The Bluetooth module is compatible with Bluetooth low energy protocol which improves battery life significantly to several weeks. The casing 104 allows the user 102 to keep track of his/her vital health data in a real time and share it to his/her family members, doctor etc. The combination of one or more sensors with an ability to track and get analytics constantly. The embodiments herein described not restricted only to sensors described above. A person having ordinary skill in the art readily understands, the casing 104 can embed with any other type of sensors also.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

The invention claimed is:

1. A casing adapted to use with a mobile device for monitoring health condition of a user, wherein said casing comprises:
    (a) a memory unit;
    (b) a sensor unit at a surface of said casing;
    (c) a plurality of health parameter measuring sensors embedded within said sensor unit for measuring raw health parameters data of said user;
    (d) a processor, which is activated from a sleep mode based on a user input comprising contacting at least one predetermined sensor surface on said casing for a predetermined period, adapted to
        (i) initialize and configure said plurality of health parameter measuring sensors; and
        (ii) receive said raw health parameters data from said plurality of health parameter measuring sensors, and
    (e) a communication unit for communicating said raw health parameters data to said mobile device for processing; and
    (f) a power unit for controllably supplying power to said plurality of health parameter measuring sensors and said processor upon detecting said user input,
    wherein said mobile device comprises a processor that
        (a) filters a baseline wandering from said raw health parameters data to obtain a filtered health parameter data;
        (b) detects a plurality of peaks that are within a predetermined peak range from said filtered health parameter data;
        (c) calculates an average interval of successive peaks of said plurality of peaks; and
        (d) calculates a heart rate of said user based on said average interval of said successive peaks.

2. The casing of claim 1, further comprising a connector port for connecting at least one external sensor to communicate with said processor.

3. A system for monitoring health condition of a user, wherein said system comprises:
    (a) a casing comprising:
        (i) a memory unit;
        (ii) a sensor unit at a surface of said casing;
        (iii) a plurality of health parameter measuring sensors embedded within said sensor unit for measuring raw health parameters data of said user, wherein said plurality of health parameter measuring sensors comprise:
            (a) a temperature sensor,
            (b) Electrocardiogram (ECG) electrodes, and
            (c) a blood oxygen level measuring sensor, and
        (iv) a processor, which is activated from a sleep mode based on a user input comprising contacting at least one predetermined sensor surface on said casing for a predetermined period, adapted to
            (a) initialize and configure said plurality of health parameter measuring sensors; and
            (b) receive said raw health parameters data from said plurality of health parameter measuring sensors, and
        (v) a communication unit for communicating said raw health parameters data, and
        (vi) a power unit for controllably supplying power to said plurality of health parameter measuring sensors and said processor upon detecting said user input; and
    (b) a mobile device adapted to use with said casing, wherein said mobile device comprises:
        (i) a memory unit comprising a database and a set of modules; and
        (ii) a processor that executes said set of modules, wherein said set of modules comprise:
            (a) a raw health parameters data receiving module, executed by said processor of said mobile device, that receives said raw health parameters data from said communication unit; and
            (b) a raw data processing module comprising an ECG data processing module that
                (a) filters baseline wandering from said raw health parameters data to obtain a filtered health parameter data;
                (b) detects a plurality of peaks that are Within a predetermined peak range from said filtered health parameter data;
                (c) calculates an average interval of successive peaks of said plurality of peaks; and
                (d) calculates a heart rate of said user based on said average interval of said successive peaks.

4. The system of claim 3, wherein said set of modules further comprise an oxygen saturation computing module that
    (a) obtains photoplethysmogram (PPG) data comprising signals from an infrared light emitting diode and a red light emitting diode from said communication unit;

(b) determines a peak buffer containing peaks of said PPG data;
(c) calculates a peak to peak amplitude of values sampled by a photodiode; and
(d) determines saturation of peripheral oxygen (Spo2) based on said peak to peak amplitude.

5. The system of claim 3, wherein said set of modules further comprise a respiration data processing module that processes said PPG data or ECG data and measures respiration characteristic of said user.

6. The system of claim 3, wherein said set of modules further comprise a temperature computing module that computes skin temperature of said user from said raw health parameters data comprising voltage values.

7. The system of claim 3, wherein said casing further comprises a connector port for connecting at least one external sensor to communicate with said processor.

8. The system of claim 3, wherein said casing is in a form of a wrist watch, a band, or a cover.

9. A method for monitoring health condition of a user using a casing adapted to use with a mobile device, said method comprising:
(i) obtaining, by a processor of said casing, a user input comprising contacting at least one predetermined sensor surface on said casing for a predetermined period;
(ii) activating said processor of said casing from a sleep mode based on said user input;
(iii) initializing and. configuring, by said processor of said casing, a plurality of health parameter measuring sensors which is embedded with said casing;
(iv) measuring, by said plurality of health parameter measuring sensors, raw health parameters data of said user;
(v) receiving, by said processor of said casing, said raw health parameters data from said plurality of health parameter measuring sensors;
(vi) communicating, by a communication unit, said raw health parameters data to said mobile device for processing;
(vii) filtering, by a processor of said mobile device, baseline wandering from said raw health parameters data to obtain a filtered health parameter data;
(viii) detecting, by said processor of said mobile device, a plurality of peaks that are within a predetermined. peak range from said. filtered. health parameter data;
(xi) calculating, by said processor of said mobile device, an average interval of successive peaks of said plurality of peaks; and
(x) calculating, by said processor of said mobile device, a heart rate of said user based on said average interval of said successive peaks.

10. The method of claim 9, further comprising connecting at least one external sensor to said processor through a connector port.

11. The method of claim 9, further comprising:
(a) obtaining photoplethysmo gram (PPG) data from said communication unit;
(b) determining a peak buffer containing peaks of said PPG data;
(c) calculating a peak to peak amplitude of values sampled by a photodiode; and
(d) determining saturation of peripheral oxygen (SpO2) based on said peak to peak amplitude.

12. The method of claim 11, further comprising processing said PPG data or ECG data and measuring respiration characteristic of said user.

13. The method of claim 11, further comprising computing skin temperature of said user from said raw health parameters data comprising voltage values.

* * * * *